United States Patent
Cohen et al.

(12) 
(10) Patent No.: US 6,513,682 B1
(45) Date of Patent: Feb. 4, 2003

(54) DISPENSING PUMP ACCESSORIES FOR PREVENTING THE INGRESS OF AIR AND FOR AIDING IN ALIGNMENT

(75) Inventors: Ben Z. Cohen, 140 E. 80th St., New York, NY (US) 10021; Nigel Kelly, Rye, NY (US)

(73) Assignee: Ben Z. Cohen, New York, NY (US)

( * ) Notice: Subject to any disclaimer, the term of this patent is extended or adjusted under 35 U.S.C. 154(b) by 0 days.

(21) Appl. No.: 09/806,394

(22) PCT Filed: Sep. 29, 2000

(86) PCT No.: PCT/US99/22511
§ 371 (c)(1),
(2), (4) Date: May 29, 2001

(87) PCT Pub. No.: WO00/18679
PCT Pub. Date: Apr. 6, 2000

Related U.S. Application Data

(60) Provisional application No. 60/102,265, filed on Sep. 29, 1998.

(51) Int. Cl.[7] .............................. B67D 5/40; B67D 47/18
(52) U.S. Cl. ........................ 222/385; 222/158; 222/420
(58) Field of Search .............................. 222/385, 383.1, 222/372, 420, 158

(56) References Cited

U.S. PATENT DOCUMENTS

| | | | |
|---|---|---|---|
| 2,693,899 A | * 11/1954 | Trout | 222/341 |
| 3,168,913 A | * 2/1965 | Eagles | 141/23 |
| 5,030,214 A | 7/1991 | Spector | 604/301 |
| 5,038,964 A | 8/1991 | Bouix | 222/153 |
| 5,244,122 A | 9/1993 | Botts | 222/133 |
| 5,875,925 A | 3/1999 | Stevens | 222/67 |
| 5,881,956 A | * 3/1999 | Cohen et al. | 222/321.7 |
| 5,934,519 A | 8/1999 | Kim et al. | 222/464.4 |

* cited by examiner

Primary Examiner—Henry C. Yuen
Assistant Examiner—Stephanie L. Willatt
(74) Attorney, Agent, or Firm—Hoffmann & Baron, LLP

(57) ABSTRACT

Accesories are provided for preventing the ingress of air into a dispensing pump (P) and to align a discharge aperture of the dispensing pump with a target, such as an eye (E). A dispensing pump (P) includes a pump cylinder (400) that has one end thereof in close proximity to a base (402) of a liquid reservoir (404). A capillary action is created to cause liquid (L) to be drawn into the inlet opening (406) of the pump cylinder (400).

14 Claims, 14 Drawing Sheets

DISPENSING PUMP ACCESSORIES FOR PREVENTING THE INGRESS OF AIR AND FOR AIDING IN ALIGNMENT

This application claims priority of U.S. Provisional Appl. Ser. No. 60/102,265, filed Sep. 29, 1998.

FIELD OF THE INVENTION

This invention relates to dispensing pump accessories and, more particularly, to accessories for preventing the ingress of air into a dispensing pump and for aiding in aligning the pump prior to a dispensing procedure.

BACKGROUND OF INVENTION

Dispensing pumps are known in the prior art for administering various liquids, including medicants, lotions, oils, perfumes, etc. The majority of dispensing pumps are positive displacement pumps in which the precise size of an administered dose is not considered critical. However, there is a subset of dispensing pumps that satisfy applications where the dose size is considered critical and repeated consistent dosing within narrow tolerances is required. For example, in U.S. Pat. No. 5,881,596 entitled "MICRODISPENSING OPHTHALMIC PUMP" which issued on Mar. 16, 1999 to the inventors herein, discloses a pump capable of repeatedly delivering doses as small as 5 microliters. Wherever repeated consistent dosing is required, especially with microdoses, such as that delivered by the pump of U.S. Pat. No. 5,881,596, the ingress of air into the pump mechanism and/or liquid path through the pump may cause dosing irregularity and/or pump stalling. The harmful effects of the ingress of air stem largely from its compressibility. If excessive air is introduced, the pump may require re-priming, which is not desirable, or may be impossible. Even where pumps are insensitive to this problem because the dose volume is sufficiently large that delivery of a dose will cause the an to be purged, the dose volume is nevertheless affected and this is undesirable in certain instances.

A common cause of the ingress of air into a dispensing pump is the exposure of an inlet end of a dip tube to air entrapped in a liquid reservoir. The inlet end is exposed generally because the dispensing pump is oriented in a gravitationally non-upright position and/or a low level of liquid is present in the reservoir.

Separately, with the majority of dispensing pumps, the alignment of the dispensing pump and a target is not critical. There are, nevertheless, devices that require to be carefully aligned with a target prior to delivery of a dose. For example, the pump of U.S.Patent No. 5,881,596 is capable of delivering a dose of ophthalmic medication to an eye. The alignment of the eye, in particular a portion to be treated (e.g., iris, pupil, cornea), with the dispensing pump is an important factor in maximizing the effectiveness of the medication.

It is an object of the subject invention to provide accessories for a dispensing pump which will prevent the ingress of air thereinto.

It is also an object of the subject invention to provide accessories for aiding in the alignment of the dispensing pump prior to actuation of the dispensing pump, and delivery of a dose.

SUMMARY OF THE INVENTION

The aforementioned objects are met by a variety of accessories for a dispensing pump.

To prevent the ingress of air into a dispensing pump, in a first embodiment of the invention, a sealed dip tube is provided to replace the liquid reservoir of a dispensing pump. In particular, a dip tube having an elongated member with two ends and an inner passage extending therebetween is provided, in which a liquid supply for the dispensing pump is disposed in the passage. A sealing plug is located in the passage so as to prevent the ingress of air into the liquid. In a preferred embodiment, the sealing plug is slidable in the passage, so as liquid is drawn from the passage, the plug slides behind the liquid as it is drawn and reduces the volume of the passage that is in communication with the dispensing pump. With the arrangement of the first embodiment, the dip tube takes the place of the reservoir, and reduces the likelihood of ingress of air into the pump.

In a second embodiment of the invention, a pliant dip tube is provided to which is mounted an anchor. The pliancy of the dip tube, and the weight of the anchor, cause the dip tube to be responsive to gravitational orientation of the dispensing pump. Thus, for example, where the pump is held upside down (i.e. the nozzle is gravitationally lower than the reservoir), the dip tube is bent by the weight of the anchor to have the inlet thereof be directed downwardly and into communication with the liquid. As such, the likelihood of exposing the inlet of the dip tube to air is reduced. In a normal prior art arrangement, the dip tube is formed stiff and is not weighted. Thus, a prior art dip tube is not generally responsive to shifts in gravitational orientation of the liquid contained in the dispensing pump reservoir. It is also preferred that the anchor have sufficient weight to ensure that the inlet of the dip tube is submerged in the liquid at all orientations of the dispensing pump.

In a third embodiment of the invention, a liquid reservoir is provided which is preferably cup-shaped with a base and an upstanding side wall. A recess is defined in the base of the reservoir, into which an inlet end of a dip tube extends. The dip tube serves to communicate liquid accommodated in the recess with a dispensing pump. Additionally, a semi-permeable membrane extends across the recess. With the dispensing pump in a gravitationally upright position, liquid contained in the reservoir seeps through the membrane to flood the recess. Upon actuation of the dispensing pump, liquid is drawn through the dip tube from the recess. If the dispensing pump is held in a non-upright position, the semi-permeable membrane restricts flow of the liquid out of the recess—albeit the restriction is not absolute, and liquid eventually seeps through the membrane. The restriction of the semi-permeable membrane, however, makes available a liquid supply for a dose of liquid to be administered by the dispensing pump, with the dispensing pump having any orientation, although the supply will be maintained for a limited time (i.e., before all of the liquid seeps out of the recess). With this arrangement, a volume of liquid is maintained, at least for a limited time, about the inlet end of the dip tube in any orientation of the dispensing pump, so as to limit the ingress of air into the dispensing pump.

A safety is provided as a fourth embodiment of the invention. In U.S. Pat. No. 5,881,596, a gravity sensitive failsafe mechanism is disclosed in which a dispensing cap and an actuator coact to prevent actuation of the pump with the discharge aperture being oriented outside a predetermined angular range of operation. Although this arrangement is very effective, the inclusion of the actuator as an additional structural element in a dispensing pump may not be desired. With the fourth embodiment of the subject invention, the safety comprises a safety ball; a blind aperture formed in the underside of a nozzle cap with the blind aperture preferably facing in the actuation direction; and, a conical depression partially in registration with the blind aperture that is defined in the dispensing pump body. The safety ball is disposed in the conical depression, and the conical depression is formed such that when a discharge aperture defined in the nozzle cap is oriented beyond a predetermined angular range of operation, the safety ball is urged out of registration with the blind aperture, and when the discharge aperture is oriented within the predetermined angular range of operation, the safety ball is urged into registration with the blind aperture. Where the safety ball is out of registration with the blind aperture, the safety ball prevents depression of the nozzle cap; conversely, where, the safety ball is in registration with the blind aperture, the nozzle cap may be depressed with the safety ball being received within the blind aperture. The predetermined angular range of operation is selected to increase the likelihood that the inlet end of a dip tube is submerged in liquid in a reservoir of the dispensing pump.

In a fifth embodiment of the invention, a dispensing pump is formed having a pump cylinder disposed partially within a reservoir, with an inlet end of the pump cylinder being in close proximity to the base of the reservoir. The inlet end of the pump cylinder includes an inlet opening which communicates the pump cylinder with liquid contained in the reservoir. No dip tube is used. By locating the inlet end of the pump cylinder in proximity to the base, capillary action of the liquid causes liquid to be drawn to the inlet end/reservoir base interface. To enhance the drawing process, the inlet end may be partially concavely curved away from the base, wherein the concavely curved portion is provided to encourage liquid at the base to feed the pump cylinder equally from all sides. It is also preferred that the pump cylinder be disposed in proximity to a portion of the side wall of the reservoir, and, specifically in proximity to the portion of the side wall located most proximally to the discharge aperture of the dispensing pump. In this manner, the tendency of a party to tilt the dispensing pump forwardly during use is taken advantage of in feeding liquid to the pump cylinder. Also, the pump cylinder/side wall interface allows for capillary action to draw fluid therein. With the dispensing pump in a non-upright position, this capillary action will cause liquid to be drawn up the pump cylinder and to the inlet end thereof. The elimination of the dip tube, and the reliance on capillary action, reduces the likelihood of air being introduced into the dispensing pump.

In a sixth embodiment of the invention, a spectacle frame, that is devoid of lenses, is provided having integrally formed therewith a holder that is formed to engage and hold a dispensing pump. The holder is located so that an engaged dispensing pump will have its discharge aperture aligned with a person's eye. The holder can be formed to allow for rotation of an engaged dispensing pump, thereby, allowing for a particular area of an eye to be targeted. Once aligned, the dispensing pump is actuated with delivery of a dose of liquid to the intended, aligned area.

In a seventh embodiment of the invention, a mirrored label is disposed about a discharge aperture of a dispensing pump. The mirrored label facilitates alignment of a portion of an eye, that is to receive a dose of liquid, with the discharge aperture of a dispensing pump.

These and other features of the invention will be better understood through a study of the following detailed description and accompanying drawings.

BRIEF DESCRIPTION OF THE DRAWINGS

In the drawing figures, which are not to scale, and which are merely illustrative, and wherein like reference numerals depict like elements throughout the several views.

DETAILED DESCRIPTION OF THE PREFERRED EMBODIMENTS

Figure 1:
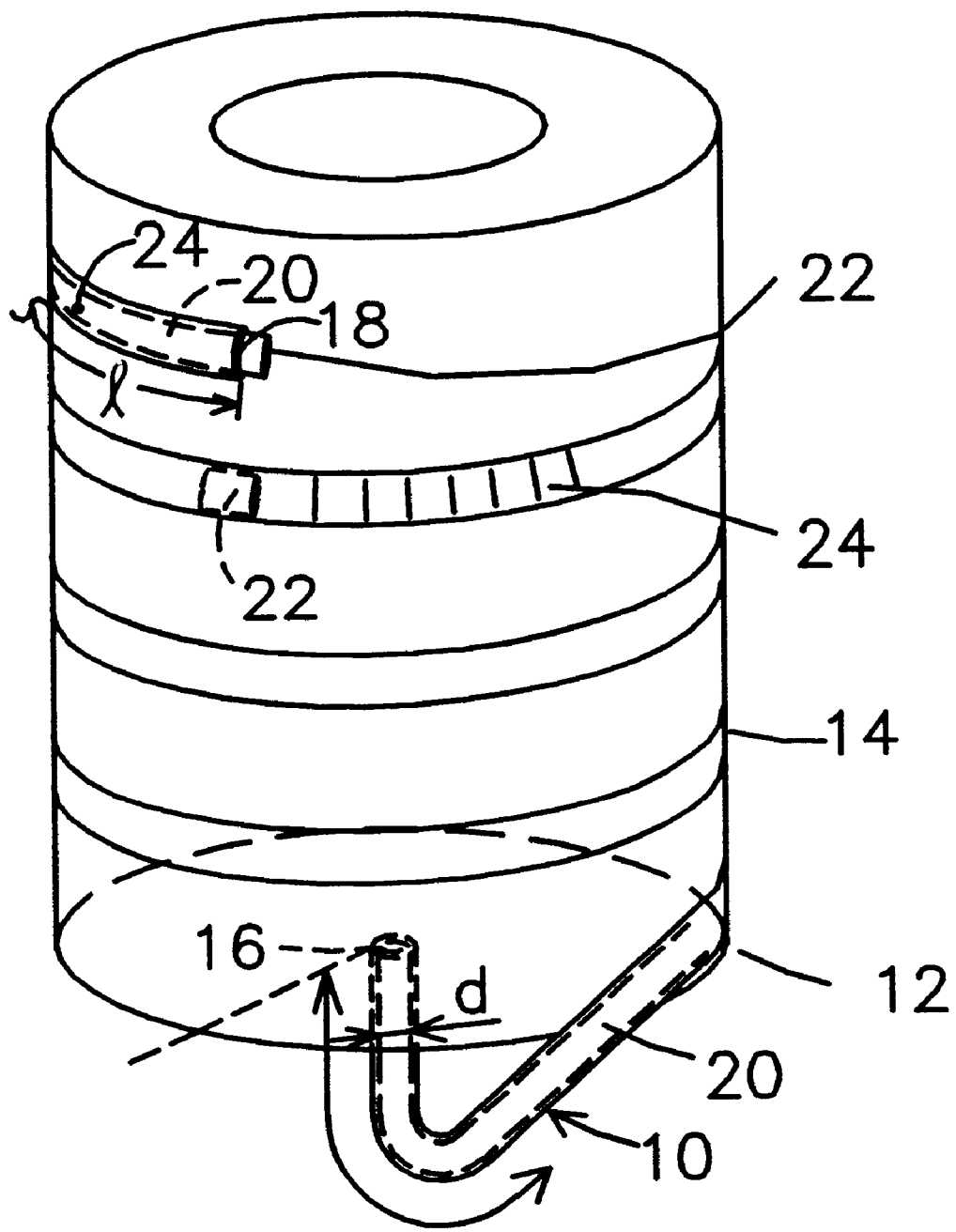
FIG. 1 is an isometric view of a dip tube of the first embodiment of the subject invention coiled about a cylinder of a dispensing pump.
Figure 2:
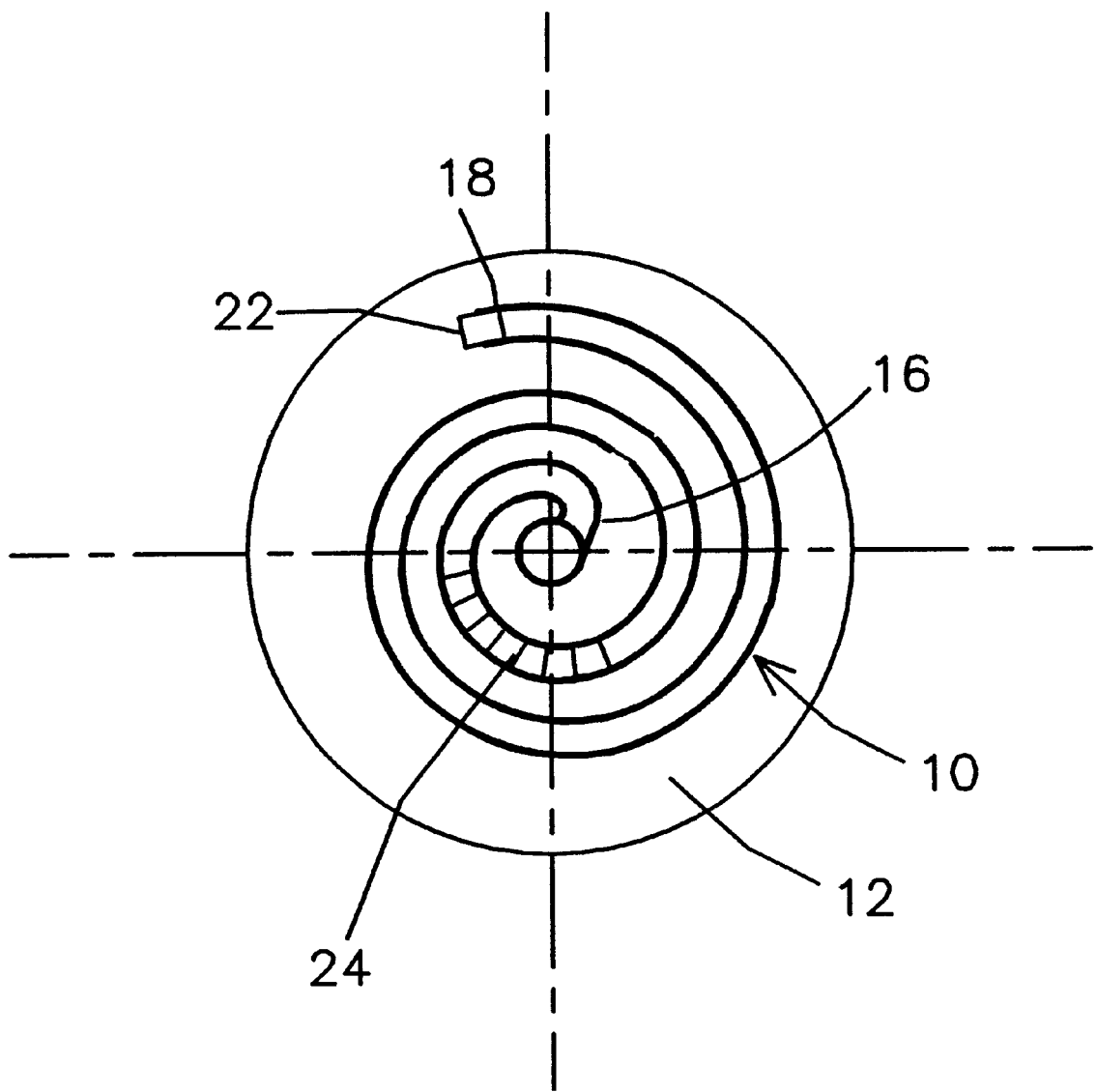
FIG. 2 is a bottom plan view of a dip tube of the first embodiment of the subject invention coiled underneath a cylinder of a dispensing pump.

In a first embodiment of the invention, referring to FIGS. 1 and 2, a dip tube 10 is provided that serves as a liquid reservoir for a dispensing pump. FIGS. 1 and 2 show only a portion of a pump cylinder 12. The pump cylinder is part of the body of a dispensing pump that at least partially houses the pumping mechanism. The dip tube 10 can be used with any dispensing pump design known in the prior art and the particulars of the dispensing pump are not critical to the practicing of the first embodiment.

The dip tube 10 is formed with an elongated body 14 and two ends 16, 18. A passage 20 extends the length of the elongated body 14 between the ends 16, 18. The passage 20 is shown in dashed lines as only partially extending from the ends 16 and 18—this is done for illustrative purposes, and the passage 20 extends fully through the elongated body 14 between the ends 16 and 18. The elongated body is very slender with the passage 20 defining an inner diameter d that is much less than the length l of the elongated body 14 (d<<l). The end 16 is formed to be connected to a dispensing pump using any technique known to those skilled in the art.

A volume of liquid is disposed in the passage 20. To prevent the liquid from seeping out of the end 18 and/or to prevent air, that passes through the end 18, from infiltrating the liquid, a sealing plug 22 is provided that is disposed in the passage 20, preferably closer to the end 18 than the end 16. As the dispensing pump draws liquid from the dip tube 10, the volume of liquid therein decreases. Accordingly, a small vent 24 may be provided in the sealing plug 22 (not shown) or the elongated body 14 that allows a limited amount of air to enter the passage 20. Alternatively, the sealing plug 22 can be sized to be slidable within the passage 20 while maintaining a seal thereabout with the passage 20. As such, the sealing plug 22 is drawn with the liquid as it is sucked from the elongated body 14. Thus, referring to FIG. 1, as shown in solid lines, the sealing plug 22 is located closer to the end 18 with a larger volume of liquid being accommodated in the passage 20 than, as shown in dashed lines, where a smaller volume of liquid is accommodated.

Figure 3:
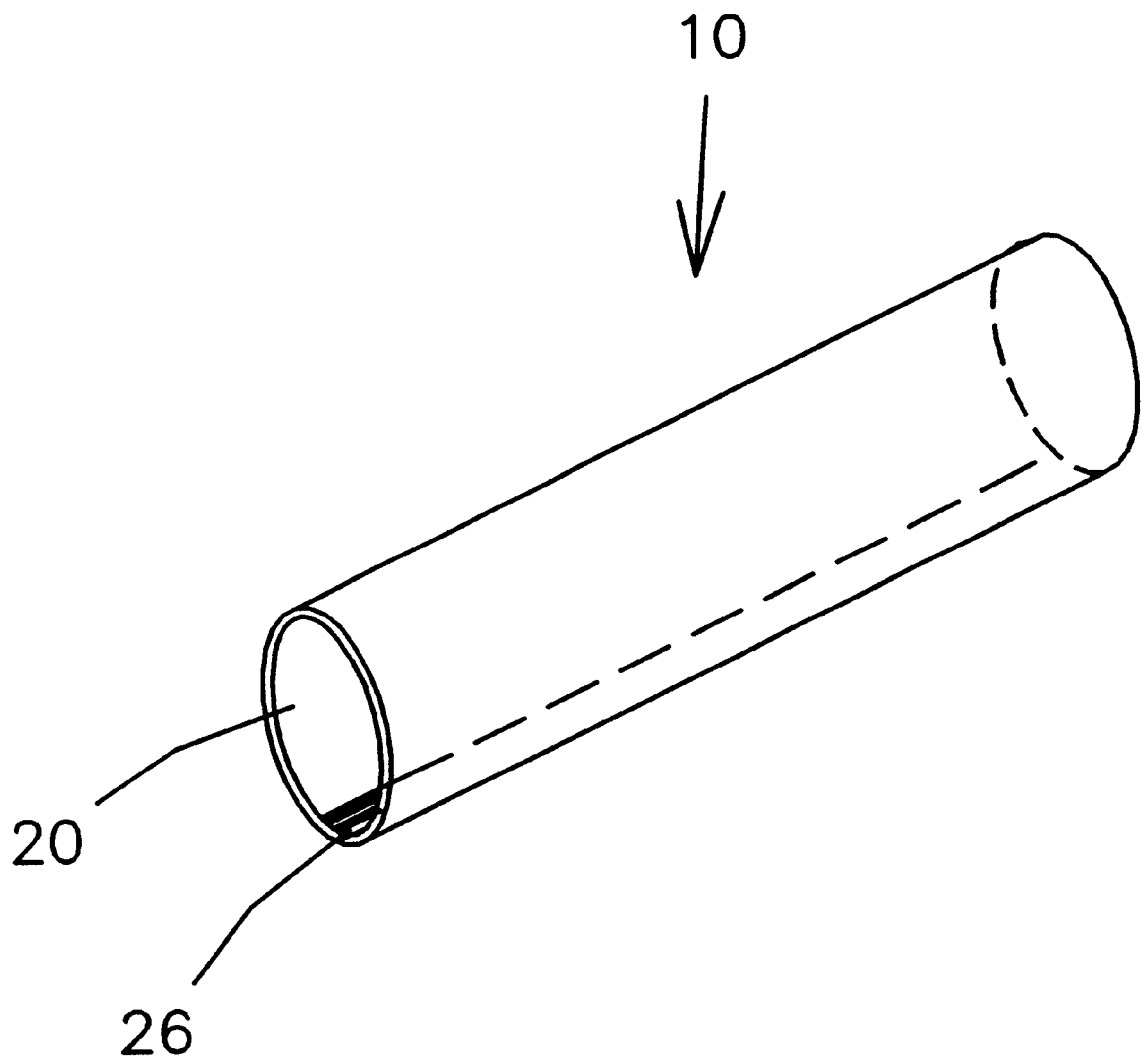
FIG. 3 is an enlarged view of a portion of a dip tube of the first embodiment with a stripe disposed thereon.

As an additional feature, the end 18 may be formed with a protruding obstruction that prevents complete, inadvertent passage of the sealing plug 22 out of the end 18. As a further feature, the elongated body 14 may be coiled about the pump cylinder 12, as shown in FIG. 1, or, as shown in FIG. 2, may be coiled therebeneath. Additionally, to assist in determining the amount of liquid in the dip tube 10, as shown in FIG. 1, graduations 24 may be inscribed on the elongated body to indicate remaining amounts of liquid volume, and/or, as shown in FIG. 3, a stripe 26 may be disposed along the length of the elongated body 14 that acts as a contrast to the liquid to allow for easy determination of liquid level. In either case, it is preferred that the graduations 24 or the stripe 26 be located at the rear of the elongated body 14 so that it is viewed through accommodated liquid—the liquid will act as a magnifying lens to broaden the indicia.

Figure 4:
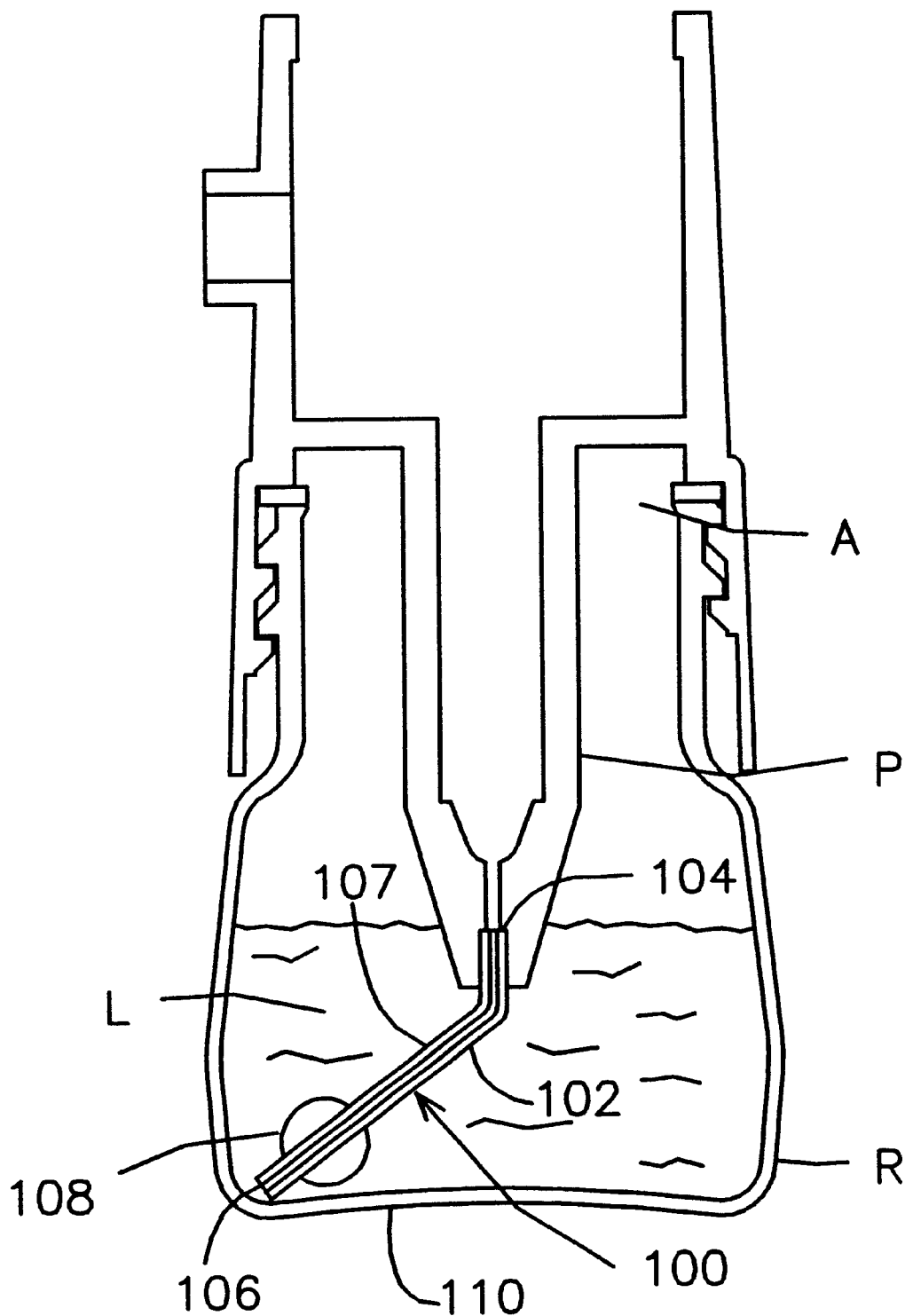
FIG. 4 is a schematic of a dip tube of the second embodiment of the subject invention mounted in an upright dispensing pump.
Figure 5:
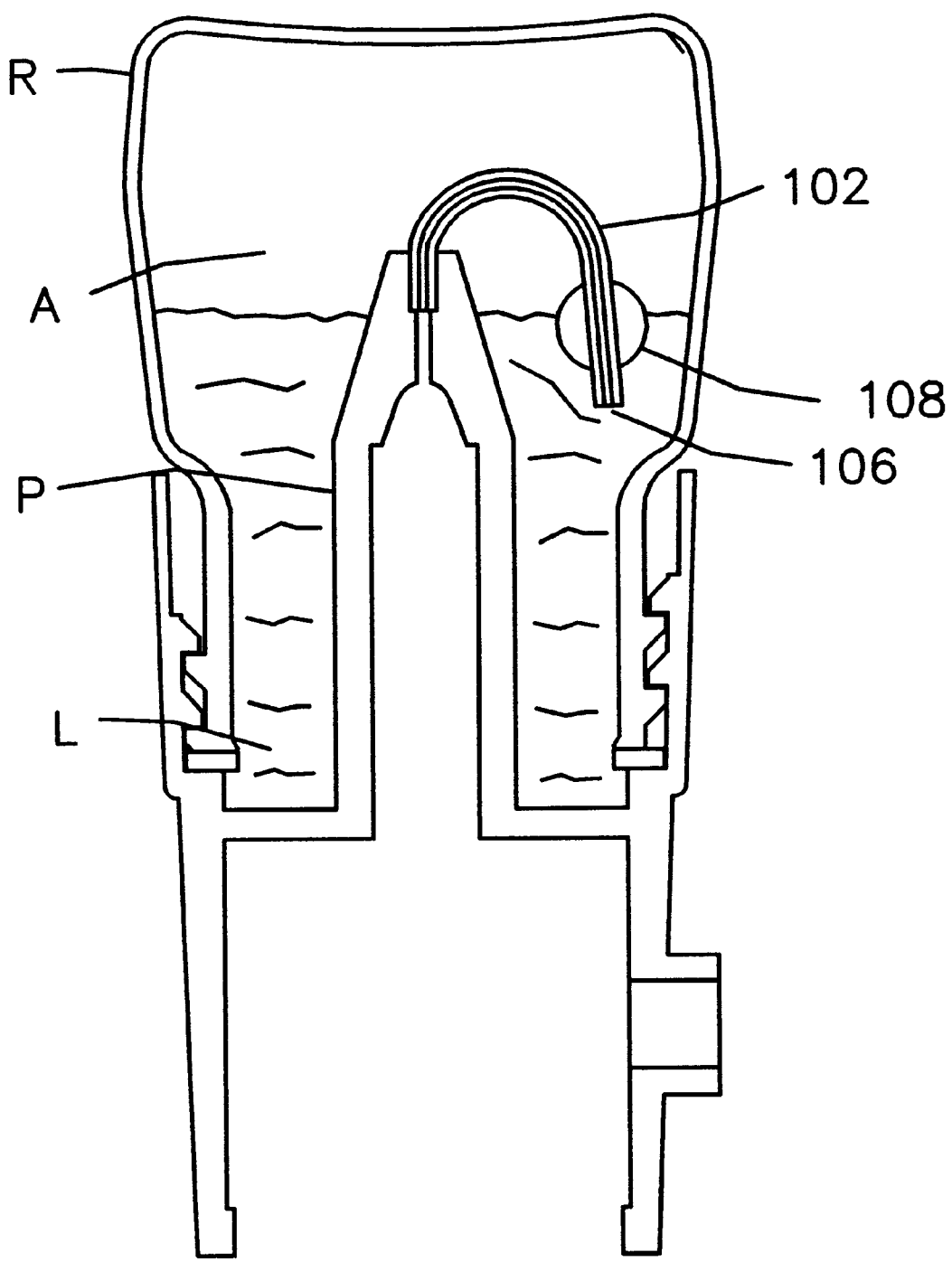
FIG. 5 is a schematic of a dip tube of the second embodiment of the subject invention mounted within an inverted dispensing pump.

In a second embodiment of the invention, a dip tube 100 is provided that is formed with an elongated, pliant body 102. The pliant body 102 includes two ends 104, 106 and a passage 107 extending therebetween through which liquid is to pass. An anchor 108 is mounted to the pliant body 102 at a location closer to the end 106 than the end 104, with the end 104 being connected to a dispensing pump P. The pliancy of the pliant body 102, and the anchor 108, cause the end 106 to be responsive to gravitational orientation of the dispensing pump P. As shown in FIG. 5, with the dispensing pump P being upside down, the pliant body 102 is bent under the weight of the anchor 108, and the end 106 is directed downwardly to be submerged within a volume of liquid L disposed in a reservoir R. The end 106 is not exposed to the air pocket A trapped in the reservoir R. In an upright position, as shown in FIG. 4, the liquid L rests on a base 110 of the reservoir R, and the end 106 is directed towards the base 110, under weight of the anchor 108. Advantageously, the second embodiment allows for responsiveness in a dip tube to gravitational orientation of the dispensing pump and the location of the liquid. Additionally, it is preferred that the anchor 108 be provided with sufficient weight to ensure that the end 106 is submerged with the liquid L.

Figure 6:
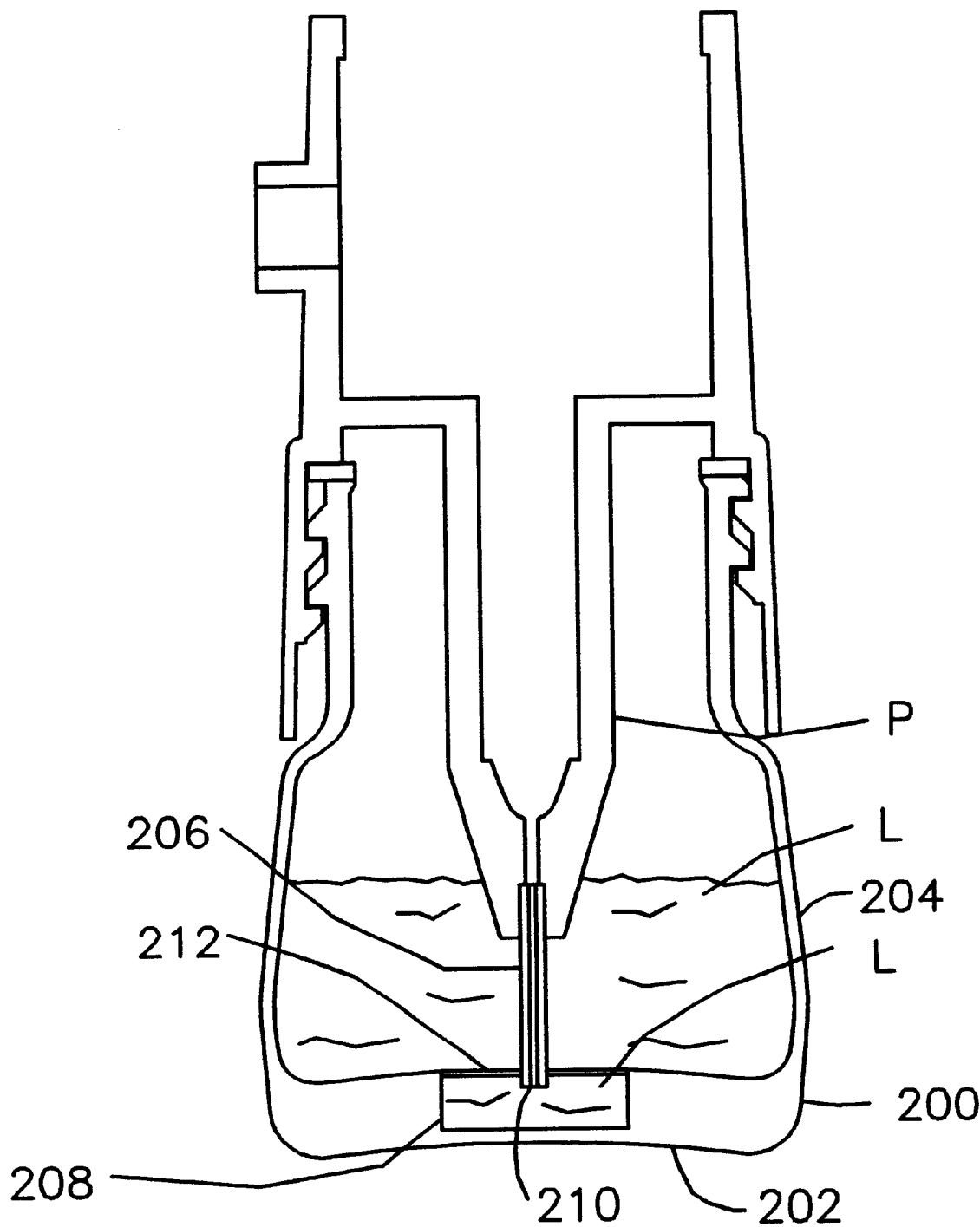
FIG. 6 is a schematic of liquid reservoir of the third embodiment of the subject invention in an upright dispensing pump.
Figure 7:
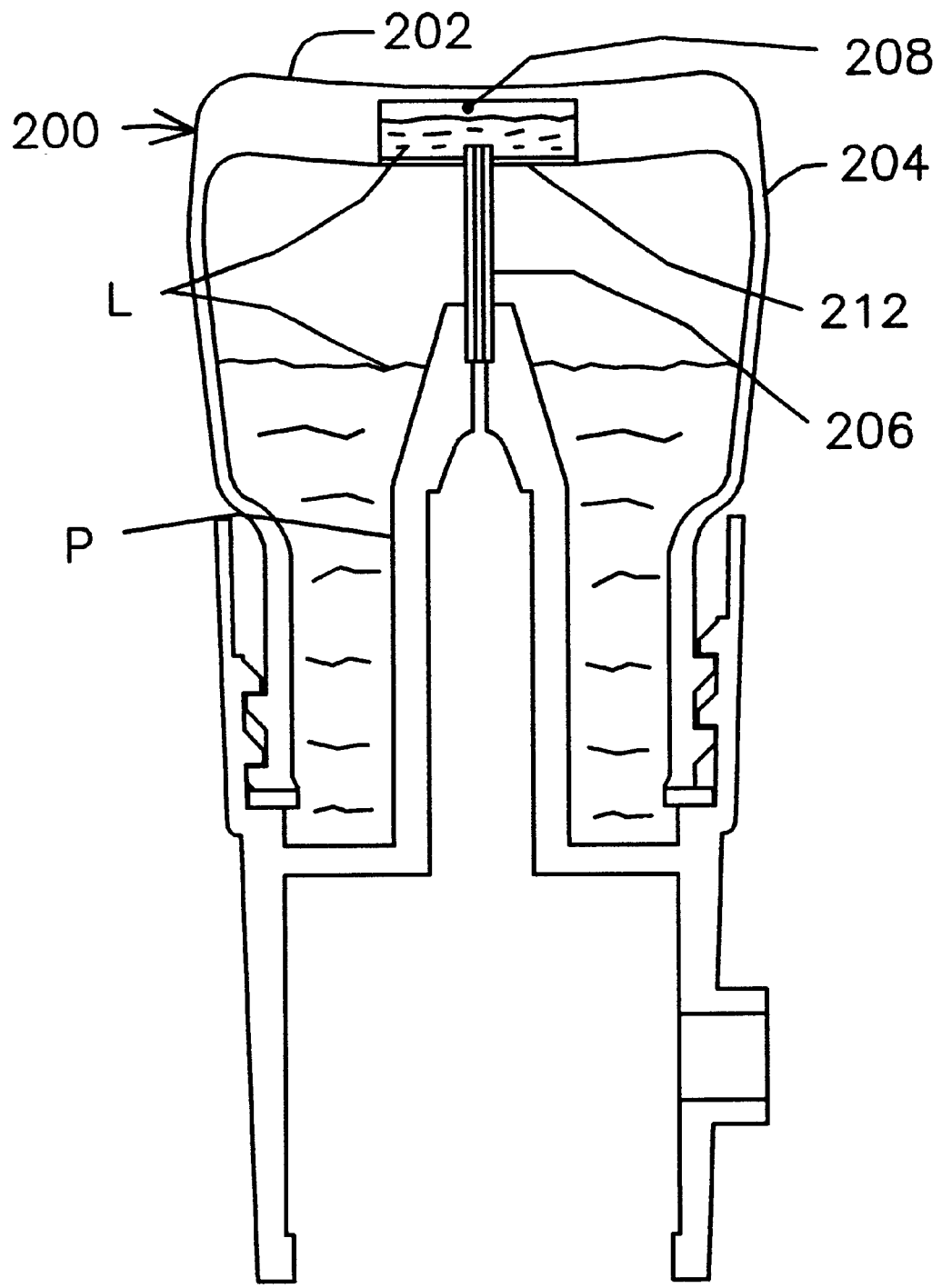
FIG. 7 is a schematic of a liquid reservoir of the third embodiment of the subject invention in an inverted dispensing pump.

Referring to FIGS. 6 and 7, a third embodiment of the invention is shown therein. Specifically, a liquid reservoir 200 is depicted having a generally cup shape with a base 202 and an upstanding side wall 204. The liquid reservoir 200 is mountable to a dispensing pump P using techniques known by those skilled in the art. A dip tube 206 is connected to the dispensing pump P to communicate liquid L disposed in the liquid reservoir 200 with the dispensing pump P.

These base 202 is formed with a recess 208. The dip tube 206 is formed with sufficient length so that an inlet end 210 extends into the recess 208. A semi-permeable membrane 212 extends across the recess 208, and about the dip tube 206. The semi-permeable membrane 212 allows the passage therethrough of the liquid L, but at a slow, seeping rate. Thus, with the dispensing pump P in an upright position as shown in FIG. 6, the liquid L rests on the base 202 and the semi-permeable membrane 212, with some of the liquid L seeping through the semi-permeable membrane 212 to flood the recess 208. With the dispensing pump P being in a non-upright position, such as the upside down position shown in FIG. 7, the liquid L located in the recess 208, and about the inlet end 210, remains there for a limited period of time (until the liquid L seeps through the semi-permeable membrane 212). The dispensing pump can be actuated in the non-upright position with liquid being drawn from the recess 208. With the third embodiment of the subject invention, a supply of liquid is maintained about the inlet of a dip tube, even though it is for a limited period, regardless of orientation of the dispensing pump. It is preferred that the volume of the recess 208 be greater than a dose of liquid that the dispensing pump P is to administer.

In a fourth embodiment of the invention, a safety is provided for increasing the likelihood that an inlet end of a dip tube, or other liquid intake, will be submerged during actuation of a dispensing pump P. In particular, the safety ensures that a discharge aperture 300 defined in a nozzle cap 302 will be oriented within a predetermined angular range of operation during actuation.

Figure 8:
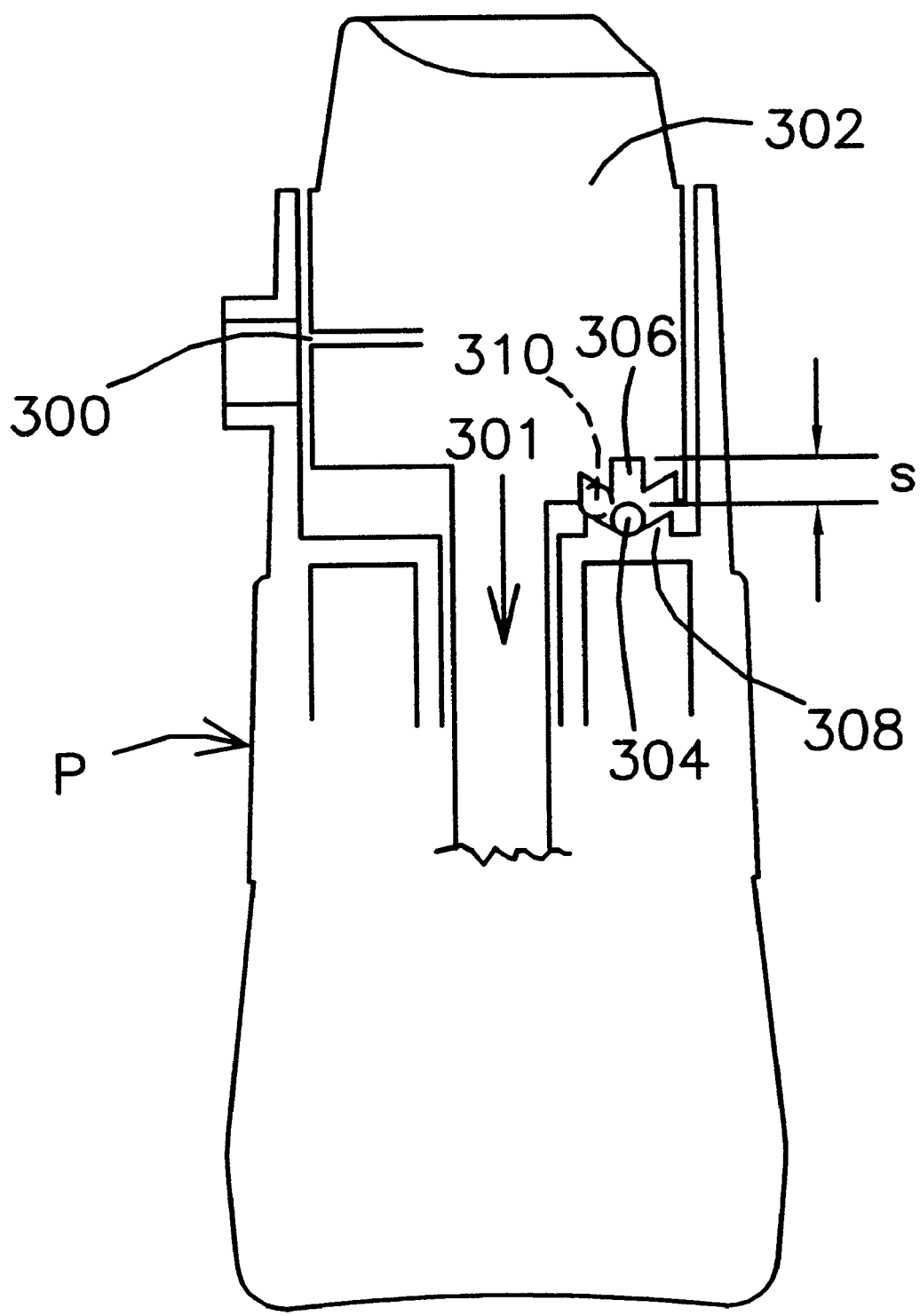
FIG. 8 is a schematic of a safety of the fourth embodiment of the subject invention.

As shown in FIG. 8, the safety comprises a safety ball 304, a blind aperture 306 formed in the underside of the nozzle cap 302, and a conical depression 308 defined in the dispensing pump P. The nozzle cap 302 is movably mounted on the dispensing pump P such that depression of the nozzle cap 302 in an actuation direction (represented by arrow 301) over stroke length S will cause actuation of the dispensing pump P and an administration of a dose of liquid from the discharge aperture 300. The blind aperture 306 is facing in the actuation direction.

The blind aperture 306 is shaped to accommodate the safety ball 304. The safety ball 304 is disposed in the conical depression 308, which has a portion thereof in registration with the blind aperture 306. The conical depression 308 is formed such that when the discharge aperture 300 is oriented within a predetermined angular range of operation, the safety ball 304 is urged into registration with the blind aperture 306, and when the discharge aperture 300 is oriented outside of the predetermined angular range of operation, the safety ball 304 is urged out of registration with the blind aperture 306. When out of registration with the blind aperture 306, the safety ball 304 prevents depression of the nozzle cap 302, and, thus, actuation of the dispensing pump P. When in registration with the blind aperture 306, the nozzle cap 302 may be depressed with the safety ball 304 being received in the blind aperture 306 and not hindering actuation of the dispensing pump P.

Figure 9A:
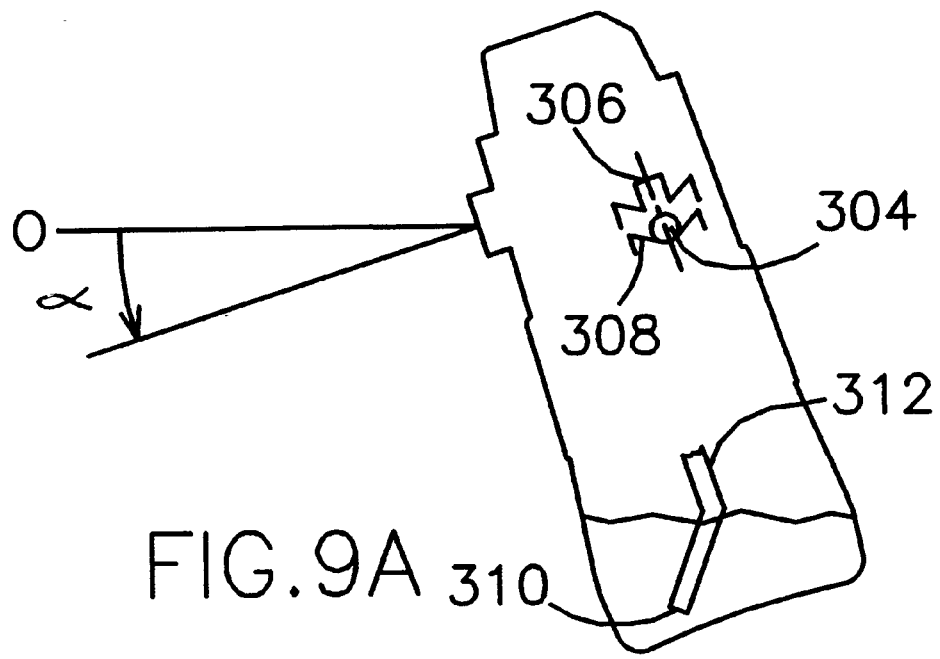
FIGS. 9A and 9B are schematics depicting angular limits of operation where the safety of the fourth embodiment of the subject invention is used with a dispensing pump.
Figure 9B:
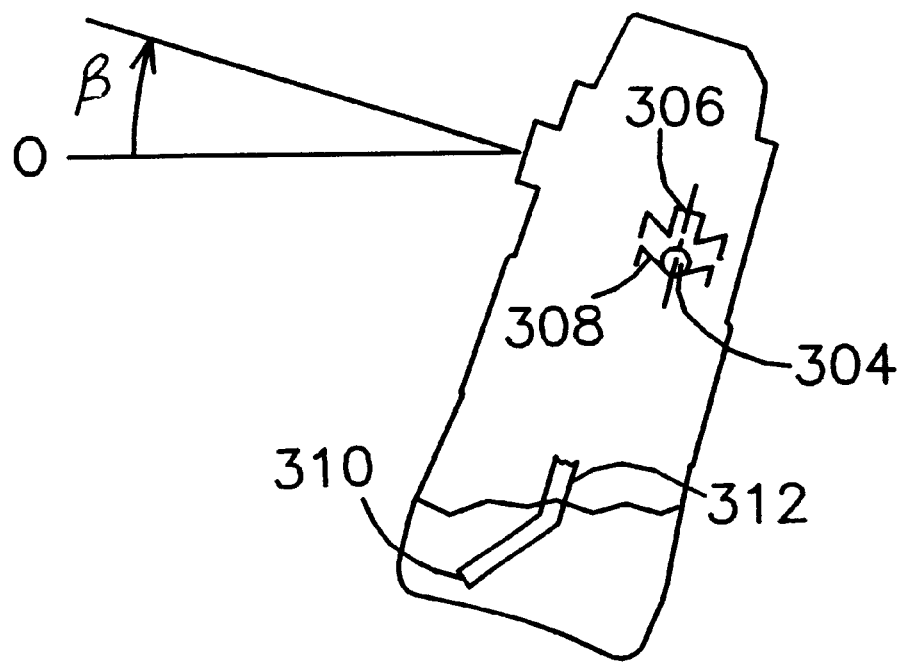

To further exemplify the fourth embodiment of the invention, reference is made to FIGS. 9A and 9B. It is assumed that the discharge aperture is at 0° in a horizontal position, angle $\alpha$ defines a lower angular limit, and angle $\beta$ defines an upper angular limit. When the discharge nozzle is oriented at either angles $\alpha$ and $\beta$, the safety ball 304 is in registration with the blind aperture 306, and thus the dispensing pump P may be actuated. At these limits, depending on the level of liquid in the reservoir, an inlet end 310 of a dip tube 312 is submerged within liquid L in the reservoir. The angular limits $\alpha$ and $\beta$ are set to obtain the greatest likelihood the inlet end 310 will be submerged within the liquid L. As is readily apparent, the inlet end 310 will not be submerged for low levels of liquid, and thus an acceptable operational level must be assumed. Beyond either angle $\alpha$ (in a counter-clockwise direction in FIG. 9A) or angle β (in a clockwise direction in FIG. 9B), the safety ball 304 is urged out of registration with the blind aperture 306. FIG. 8 shows the safety ball 304 in dashed lines in a position out of registration. When out of registration, the safety ball 304 at least partially extends from the conical depression 308 to prevent the nozzle cap 302 from traversing the fill stroke length S.

Figure 10:
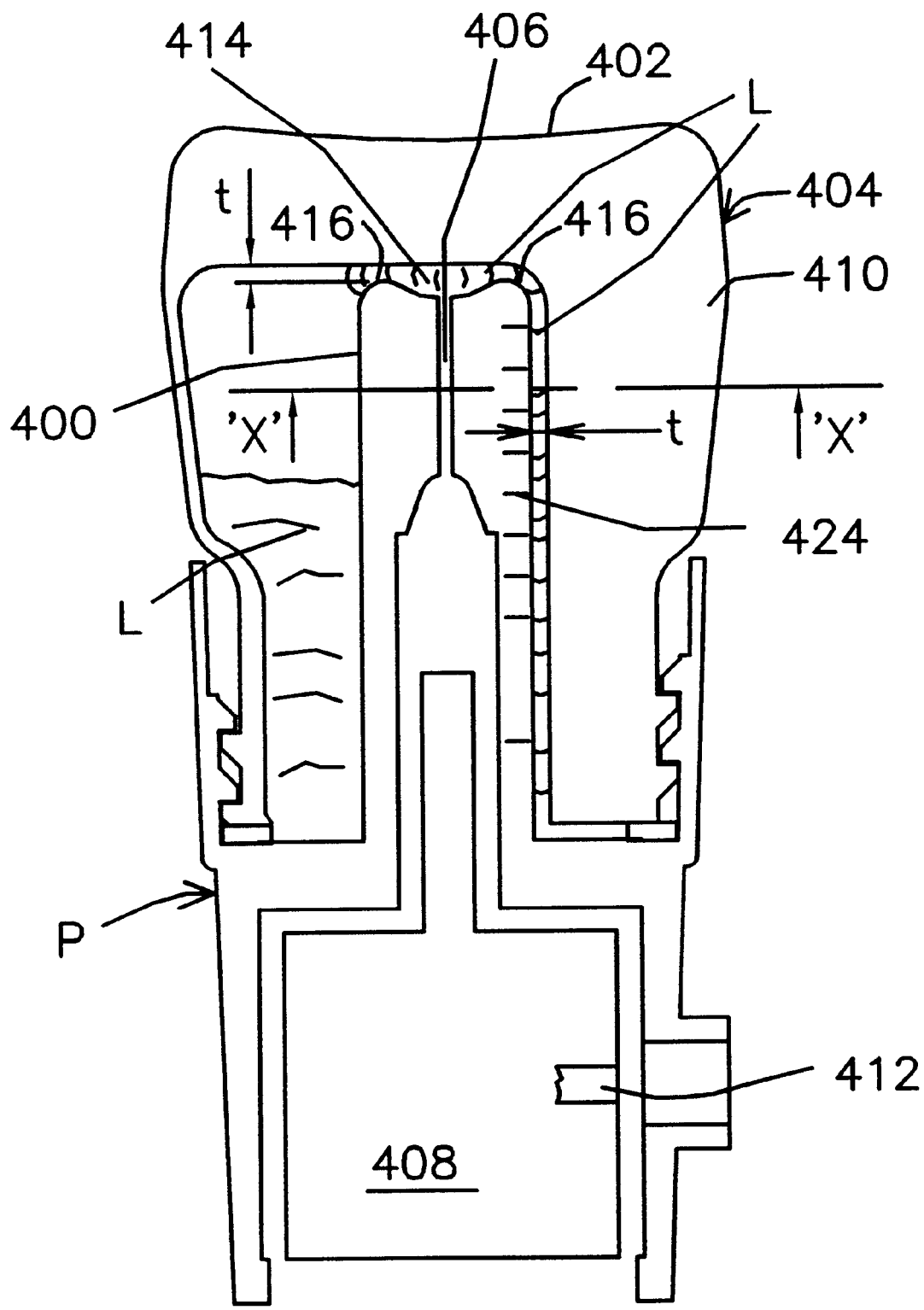
FIG. 10 is a schematic of the fifth embodiment of the subject invention with a pump cylinder being disposed in close proximity to the base of the liquid reservoir.

FIG. 10 shows a fifth embodiment of the invention which is a dispensing pump P having a pump cylinder 400 that is disposed in close proximity to a base 402 of a liquid reservoir 404. The pump cylinder 400 has an inlet opening 406 that communicates liquid L accommodated in the liquid reservoir 404 with a pumping mechanism 408. The pumping mechanism 408 can be any pump design that is known in the prior art.

As shown in FIG. 10, no dip tube is provided to communicate the liquid L with the pump cylinder 400. Rather, the pump cylinder 400 is spaced so closely to the base 402, preferably at a distance t of 0.025", or less, to rely on capillary action of the liquid L caused by the narrow spacing of the interface to draw liquid L to the inlet opening 406. The capillary action provides a sustained flow of liquid to the pump cylinder 400.

In a preferred embodiment, the pump cylinder 400 is also closely spaced to a portion of a side wall 410 of the liquid reservoir 404, preferably also at the distance t of 0.025", or less. The narrow spacing of this interface will create a capillary action that will draw liquid L between the pump cylinder 400 and the side wall 410. Advantageously, where the dispensing pump P is in a non-upright position, as shown in FIG. 10, and the inlet opening 406 is not submerged in the liquid L, the capillary action between the pump cylinder 400 and the side wall 410 will cause liquid to be drawn up the pump cylinder 400 and into the inlet opening 406. The close spacing of the pump cylinder 400 and the side wall 410 is achieved by increasing the thickness of the side wall 410. Alternatively, although not shown, the liquid reservoir 404 can be wholly offset relative to the pump cylinder 400.

The dispensing pump P is formed with a discharge aperture 412 through which liquid is dispensed. It is preferred that the pump cylinder 400 be located to the portion of the side wall 410 that is most proximal the discharge aperture 412. In this manner, the invention takes advantage of the natural tendency of a person to tilt the dispensing pump P forwardly during use, thus causing maximal collection of the liquid about the inlet opening 406. Also, it is preferred that the pump cylinder 400 be formed with a concavely curved portion 414 at the inlet opening 406. The concavely curved portion 406 increases the capillary action at the raised portions, thus improving the liquid drawing action into the pump cylinder 400. To avoid sharp edges and corners, edges 416 are convexly rounded and blended with concavely curved portion 414.

Figure 11A:
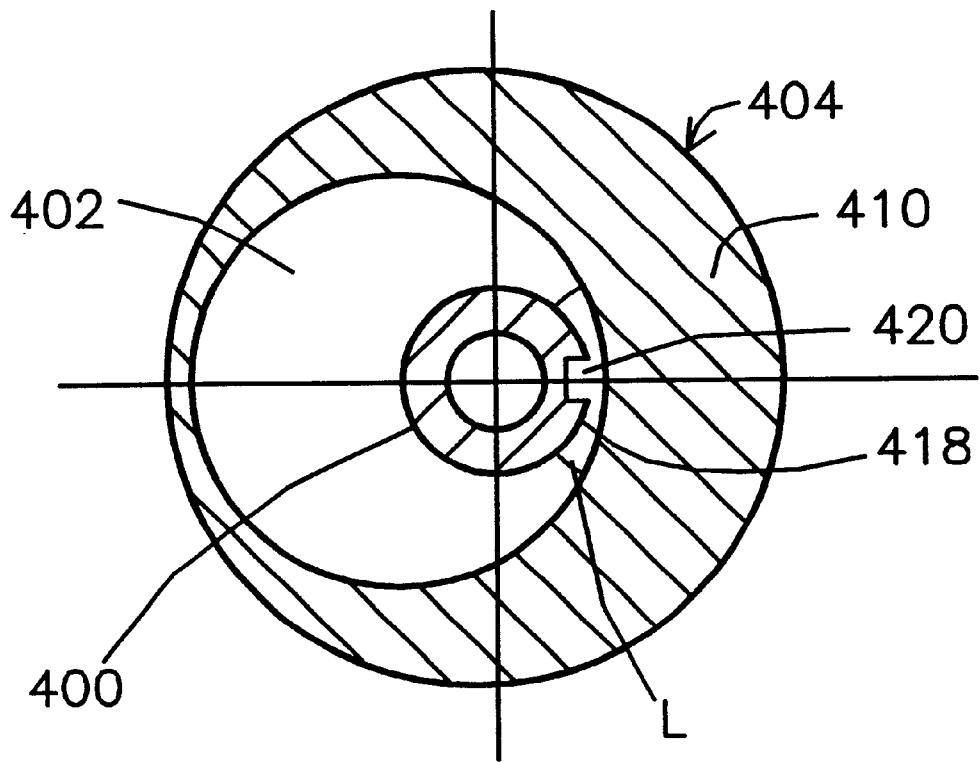
FIGS. 11A and 11B are cross-sectional views taken along line x—x of FIG. 10 showing alternate constructions of the pump cylinder.
Figure 11B:
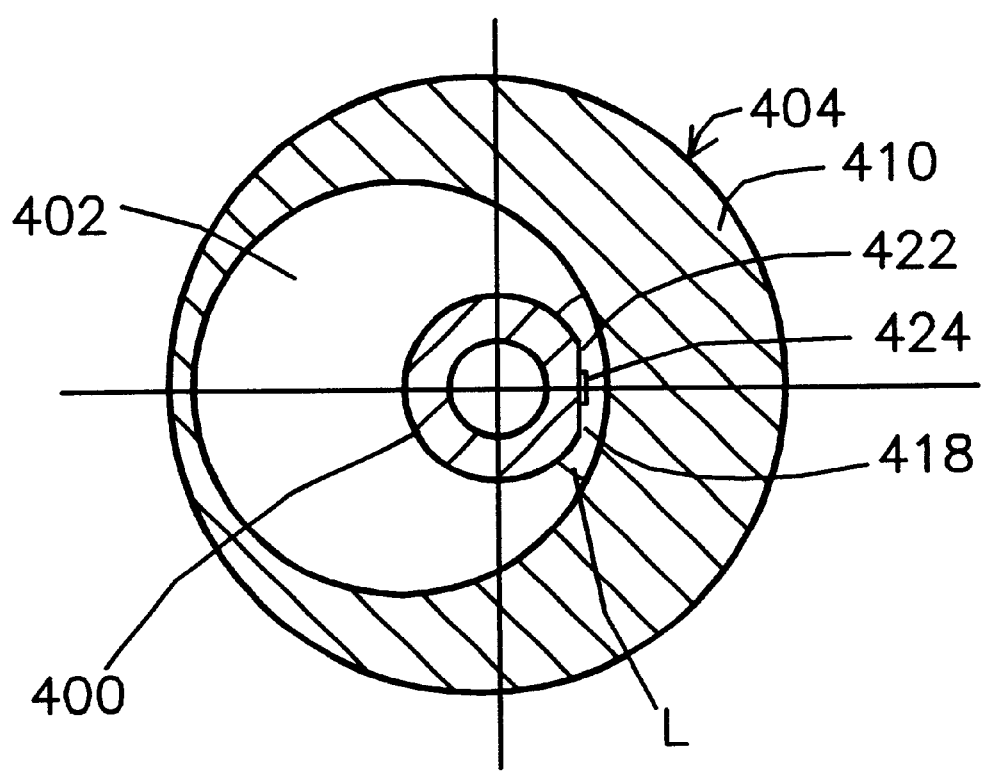

To improve the capillary action up the pump cylinder 400, as shown in FIGS. 11A and 11B, a front face 418 of the pump cylinder 400 is formed with a non-arcuate configuration, such as a groove 420 or with a flat surface 422. As an additional feature, graduations 424 may be disposed on the front face 418 to be viewable through the side wall 410 to indicate the level of the liquid L remaining in the liquid reservoir 404.

Figure 12:
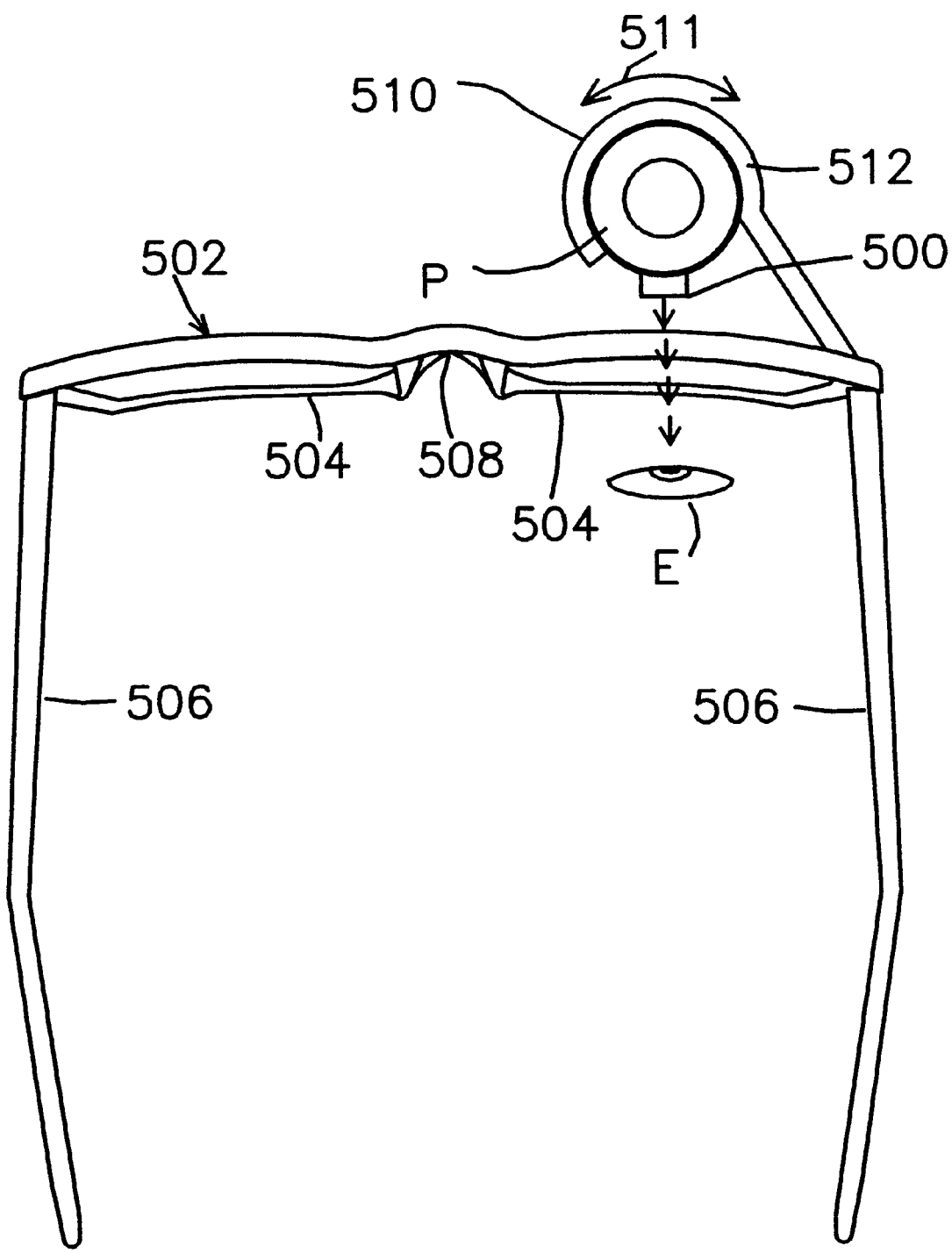
FIG. 12 is a top plan view of the sixth embodiment of the invention.
Figure 13:
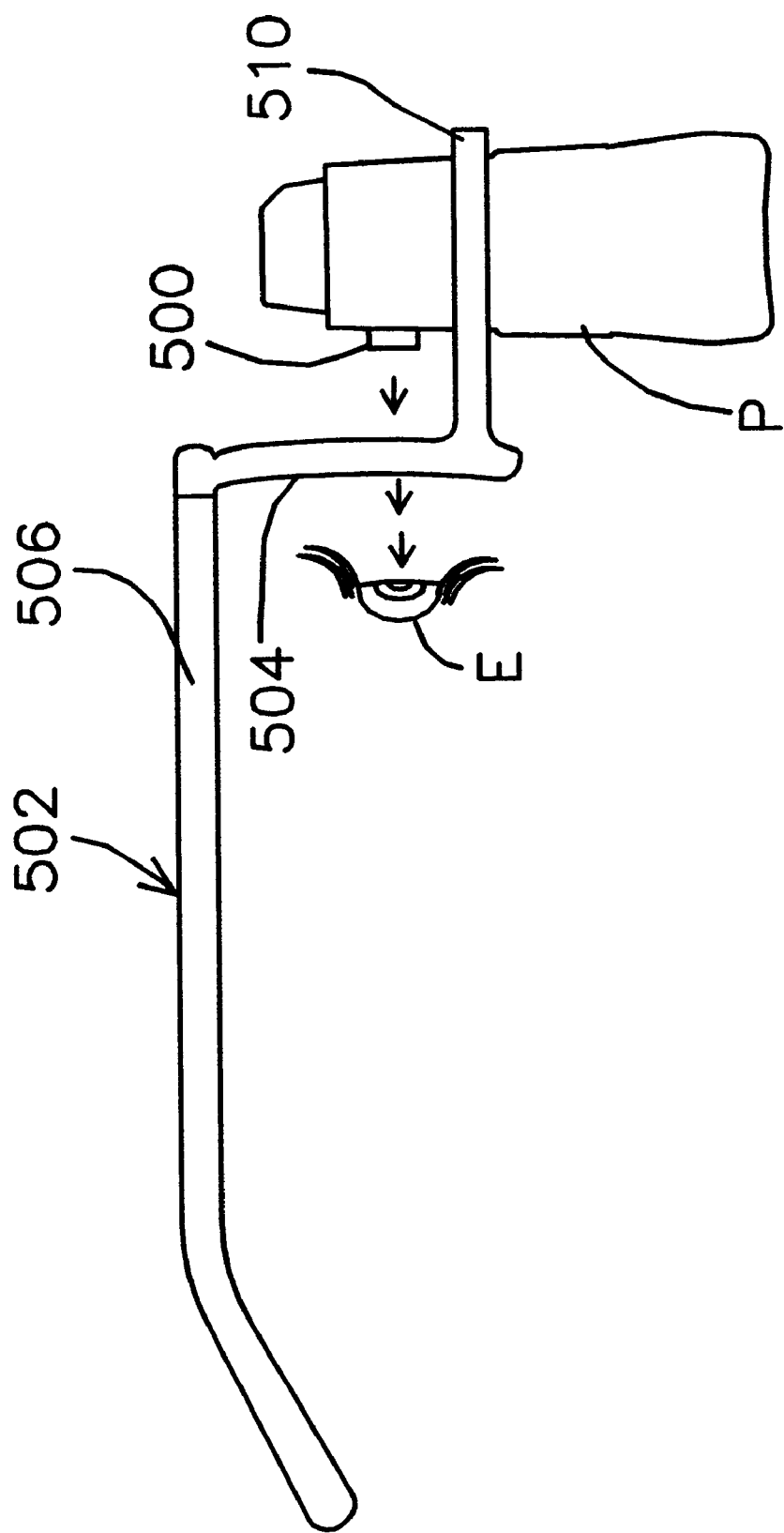
FIG. 13 is a side elevational view of the sixth embodiment of the invention; and, FIG. 14 is an isometric view of the seventh embodiment of the invention.

In a sixth embodiment of the invention, depicted in FIGS. 12 and 13, an alignment aid is provided for aligning a discharge aperture 500 of a dispensing pump P with an eye E of a patient. The alignment aid is a spectacle frame 502, formed like spectacle frames known in the prior art. Here, however, no lenses are provided. The spectacle frame 502 includes lens holder portions 504, supports 506, and a connecting bridge 508. A dispensing pump holder 510 extends from one of the lens holder portions 504, and is preferably formed integrally therewith. The dispensing pump holder 510 has a dispensing pump catch 512 that is configured to engage and hold a dispensing pump P; preferably, the catch 512 is formed to allow rotation therein of a held dispensing pump P, as represented by double-headed arrow 511. Additionally, the dispensing pump holder 510 is configured and formed such that the discharge aperture 500 of a held dispensing pump P will be aligned with the eye E, with the spectacle frame 502 being worn. Once aligned, the dispensing pump P can be actuated to administer a dose of liquid to the eye E.

Figure 14:
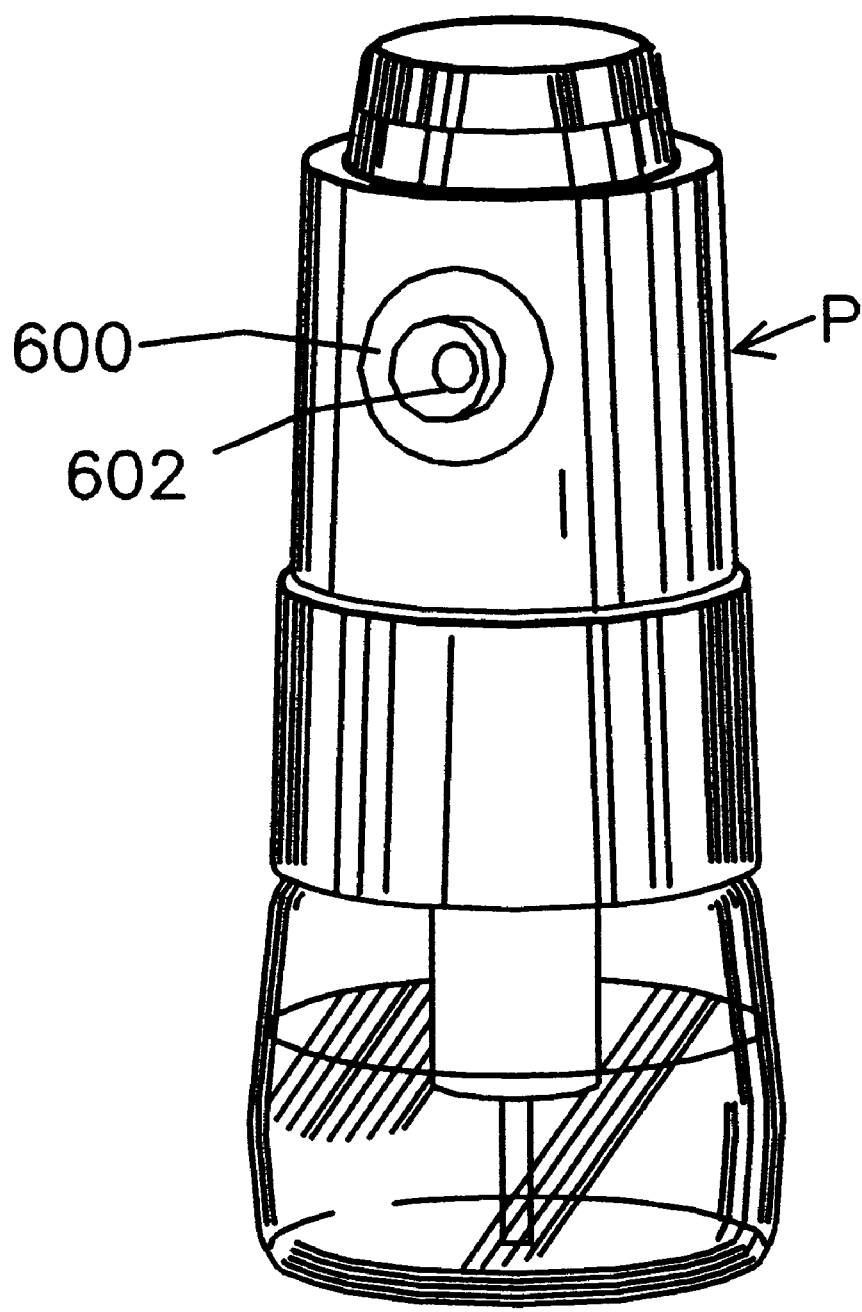

Referring to FIG. 14, in a seventh embodiment of the invention, a mirrored label 600 is provided that is sized to be mounted adjacent a discharge aperture 602 of a dispensing pump P. The mirrored label 600 is preferably annular shaped and formed with inner and outer diameters that define sufficient mirrored area for a person to view their reflection and align the discharge aperture 602 with a portion of their eye. The annular shaped mirror label 600 is mountable about the discharge aperture 602.

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

What is claimed is:

1. A dispensing pump for administering doses of liquid, said dispensing pump comprising, a pump cylinder, a pump means for administering doses of the liquid, said pump means at least partly disposed in said pump cylinder; and, a reservoir for accommodating the liquid, said reservoir being generally cup-shaped and having a base and an upstanding wall, wherein said pump cylinder having one end thereof in close proximity to said base, said pump cylinder having an opening in said one end for communicating the liquid in said reservoir with said pump means, wherein said one end being in sufficiently close proximity to said base such that capillary action of the liquid between said one end and said base acts on the liquid to draw the liquid to said opening.

2. A dispensing pump as in claim 1, wherein said pump cylinder has a front face that is disposed in proximity to a portion of said side wall.

3. A dispensing pump as in claim 2, wherein said front face is formed with a generally flat surface.

4. A dispensing pump as in claim 2, wherein said front face is formed with a groove.

5. A dispensing pump as in claim 2, wherein visible graduations are disposed on said front face so as to be visible through said side wall.

6. A dispensing pump as in claim 2, wherein said dispensing pump further includes a discharge aperture for dispensing the liquid, and wherein said front face is disposed in proximity to a portion of said side wall that is located most proximally said discharge aperture.

7. A dispensing pump as in claim 2, wherein said front face is spaced a distance of 0.025", or less, from said side wall.

8. A dispensing pump as in claim 1, wherein said one end of said pump cylinder is spaced a distance of 0.025", or less, from said base.

9. A dispensing pump as in claim 1, wherein at least a portion of said one end of said pump cylinder is curved concavely inwardly away from said base.

10. A dispensing pump as in claim 9, wherein said one end of said pump cylinder has convexly curved portions that blend with said concavely curved portion.

11. A dispensing pump for administering doses of liquid, said dispensing pump comprising, a pump cylinder, a pump means for administering doses of the liquid, said pump means at least partly disposed in said pump cylinder; and, a reservoir for accommodating the liquid, said reservoir being generally cup-shaped and having a base and an upstanding wall, wherein said pump cylinder having one end thereof in close proximity to said base, said pump cylinder having an opening in said one end for communicating the liquid in said reservoir with said pump means, wherein said pump cylinder has a front face that is disposed in proximity to a portion of said side wall, said front face being spaced a distance of 0.025", or less, from said side wall.

12. A dispensing pump for administering doses of liquid, said dispensing pump comprising, a pump cylinder, a pump means for administering doses of the liquid, said pump means at least partly disposed in said pump cylinder; and, a reservoir for accommodating the liquid, said reservoir being generally cup-shaped and having a base and an upstanding wall, wherein said pump cylinder having one end thereof in close proximity to said base, said pump cylinder having an opening in said one end for communicating the liquid in said reservoir with said pump means, wherein said one end of said pump cylinder is spaced a distance of 0.025", or less, from said base.

13. A dispensing pump for administering doses of liquid, said dispensing pump comprising, a pump cylinder, a pump means for administering doses of the liquid, said pump means at least partly disposed in said pump cylinder; and, a reservoir for accommodating the liquid, said reservoir being generally cup-shaped and having a base and an upstanding wall, wherein said pump cylinder having one end thereof in close proximity to said base, said pump cylinder having an opening in said one end for communicating the liquid in said reservoir with said pump means, wherein at least a portion of said one end of said pump cylinder is curved concavely inwardly away from said base.

14. A dispensing as in claim 13, wherein said one end of said pump cylinder has convexly curved portions that blend with said concavely curved portion.

* * * * *